United States Patent [19]

Christensen et al.

[11] Patent Number: 4,696,923
[45] Date of Patent: Sep. 29, 1987

[54] 6-[1-HYDROXYETHYL]-2-SR[8]-1-METHYL-1-CARBADETHIAPEN-2-EM-3-CARBOXYLIC ACIDS

[75] Inventors: Burton G. Christensen, Cliffside; David H. Shih, Manalapan, both of N.J.

[73] Assignee: Merck & Co., Inc., Rahway, N.J.

[21] Appl. No.: 603,036

[22] Filed: Apr. 23, 1984

[51] Int. Cl.[4] .................. C07D 487/04; A61K 31/40
[52] U.S. Cl. .................................... 514/210; 540/350
[58] Field of Search ............... 260/245.2 T; 540/350; 514/210

[56] References Cited

U.S. PATENT DOCUMENTS

| | | | |
|---|---|---|---|
| 4,232,036 | 11/1980 | Christensen et al. | 424/274 |
| 4,309,346 | 6/1982 | Christensen et al. | 260/245.2 T |
| 4,383,946 | 5/1983 | Christensen et al. | 260/245.2 T |
| 4,552,873 | 11/1985 | Miyadera et al. | 514/210 |

Primary Examiner—Nicholas S. Rizzo
Attorney, Agent, or Firm—Raymond M. Speer; Hesna J. Pfeiffer

[57] ABSTRACT

Disclosed are antibiotic 6-[1-hydroxyethyl]-2-SR[8]-1-methyl-1-carbadethiapen-2-em-3-carboxylic acids and their pharmaceutically acceptable salts and esters (I):

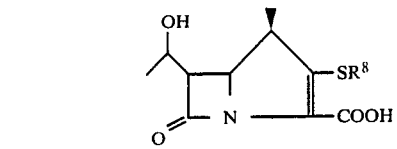

wherein: $R^8$ is

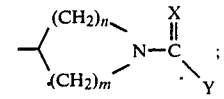

and

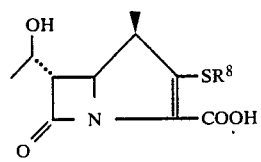

wherein: $R^8$ is

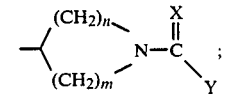

and wherein n and m are independently selected from 0, 1, 2, 3, 4 and 5; X is —NR; and Y is —R, or —NRR; and wherein R is independently selected from hydrogen, alkyl, alkenyl, alkynyl, (having 1–6 carbon atoms); cycloalkyl and cycloalkenyl (having 3–6 carbon atoms); and heterocyclyl, heteroaryl (having 3–6 ring atoms, one or more of which is N, O or S).

4 Claims, No Drawings

6-[1-HYDROXYETHYL]-2-SR⁸-1-METHYL-1-CARBADETHIAPEN-2-EM-3-CARBOXYLIC ACIDS

This invention also relates to the carboxyl derivative of I which are antibiotics and which may be represented by the following generic structure (I):

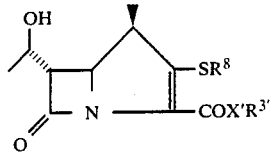

wherein X' is oxygen, sulphur or NR' (R'=H or lower alkyl having 1-6 carbon atoms); and $R^{3'}$ is, inter alia, representatively selected from the group consisting of hydrogen, conventional blocking groups such as trialkylsilyl, acyl and the pharmaceutically acceptable salt, ester and amide moieties known in bicyclic B-lactam antibiotic art; the definition of $R^{3'}$ is given in greater detail below.

This invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For, unfortunately, there is no static effectiveness of any given antibiotic, because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an objective of the present invention to provide a novel class of orally active antibiotics which are useful in animal and human therapy. These antibiotics are active against a broad range of pathogens which representatively include both gram positive bacteria such as *S. aureau, Strep. pyogenes,* and *B. Subtilis,* and gram negative bacteria such as *E. Coli, Proteus morganii, Serratia,* and *Klebsiella.* Further objects of this invention are to provide chemical processes for the preparation of such antibiotics; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention are conveniently prepared by the following scheme:

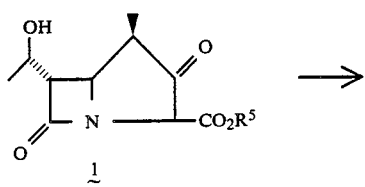

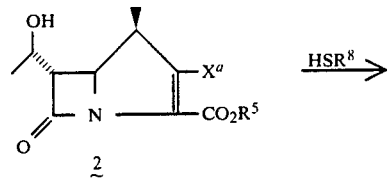

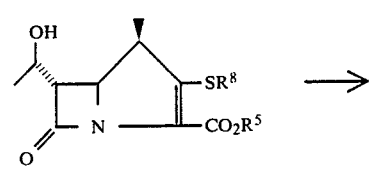

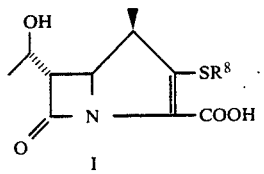

In words relative to the above reaction scheme, the step 1-2 to establish leaving group $X^a$ is accomplished by acylating the bicyclic keto ester with an acylating agent $R°X^a$ such as p-toluenesulfonic acid anhydride, p-nitrophenylsulfonic acid anhydride, 2,4,6-triisopropylphenylsulfonic acid anhydride, methane-sulfonic acid anhydride, trifluoromethane sulfonic-acid anhydride, diphenyl chlorophosphate, toluenesulfonyl chloride, p-bromophenylsulfonyl chloride, trifluoromethanesulfonyl chloride trifluoromethanesulfonic acid anhydride or the like wherein $X^a$ is the corresponding leaving group such as toluene solfonyloxy, p-nitrophenylsulfonyloxy, diphenylphosphoryl, and other leaving groups which are established by conventional procedures and are well known in the art. Typically, the above acylation to establish leaving groups $X^a$ is conducted in a solvent such as methylene chloride, acetonitrile or dimethylformiamide, in the presence of a base such as diisopropylethylamine, triethylamine, 4-dimethylamino-pyridine or the like at a temperature of from 31 20° to 40° C. for from 0.1 to 5 hours. The leaving group $X^a$ of intermediate 2 can also be halogen. The halogen leaving group is estalbished by treating 1 with a halogenating agent such as $Ø_3PCl_2$, $Ø_3PBr_2$, $(ØO)_3PBr_2$, oxalyl chloride or the like in a solvent such as $CH_2Cl_2$, $CH_3CN$, THF, or the like in the presence of a base such as diisopropylethylaime, triethylamine, or 4-dimethylaminopyridine or the like. [Ø=phenyl.]

The reaction 2 to 3 is accomplished by treating 2 in a solvent such as dioxane, dimethylformamide, dimethylsulfoxide, acetonitrile, hexamethylphosphoramide, or the like in the presence of an approximately equivalent to excess of the mercaptan reagent $HSR^8$, wherein $R^8$ is as defined above, in the presence of a base such as sodium hydrogen carbonate, potassium carbonate, triethylamine, diisopropylethylamine, or the like at a temperature of from −40° to 25° C. for from 1 min. to 72 hours.

The class of suitable $HSR^8$ reagents is representatively described below and in the Examples.

The final deblocking step 3 I is accomplished by conventional procedures such as solvolysis or hydrogenation.

Typically 3 in a solvent such as tetrahydrofuran-water, tetrahydrofuran-ethanol-water, dioxane-water, dioxane-ethanol-water, or the like containing pH 7 morpholinopropanesulfonic acid buffer, pH 7 phosphate buffer, dipotassium hydrogen phosphate, sodium bicarbonate, or the like is treated under a hydrogen pressure of from 1 to 4 atmospheres in the presence of a catalyst such as platinum oxide, palladium on charcoal, or palladium hydroxide, or the like at a temperature of from 0° to 50° C. for from 0.25 to 4 hours to provide I. Photolysis, when $R^5$ is a group such as o-nitrobenzyl, for example, may also be used for deblocking.

Relative to the above scheme, the bicyclic keto ester 1 is known. See European Patent Application (Case 16577IA) No. 81110531.1, which is incorporated herein by reference.

HSR$^8$ REAGENTS

Relative to the foregoing description of the invention, suitable reagents, HSR$^8$, which are utilized in the transformation 2 to 3 are listed below. The list is arranged according to structural and functional characteristics of the thia side chain —SR$^8$; annotation is provided where necessary. The thia side chain of choice —SR$^8$ is derived from the corresponding mercaptan reagent HSR$^8$, and thus the following list serves to further, specifically disclose —SR$^8$ side chains of I which are of special interest. When the mercaptan contains a functional group which might interfere with the intended course of reaction, the offending group is covered. For example, when a basic nitrogen group is encountered (—NHR or —NH$_2$, for example) it is usually protected by esterification (e.g., PNB ester). Such protection also facilitates in the purification of products by chromatographic means. (PNB is p-nitrobenzyl.) Such protection is, however, not a necessary requirement for introduction of the —SR$^8$ side chain. The transformation 2 to 3 above is conveniently carried out using both protected and unprotected HSR$^8$ forms.

It is recognized that SR$^8$ side chains in which the R$^8$ group contains one or more chiral centers can be added as racemic or diastereomeric mixtures to provide mixtures of diastereomeric products or can be added as resolved, isomerically pure reagents to provide diastereomerically pure products. Since antibacterial activity and other pharmacological properties vary among isomers, it is frequently advantageous to prepare isomerically pure products by the introduction of resolved —SR$^8$ side chains.

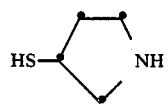

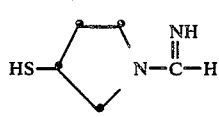

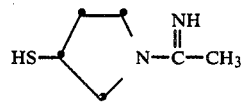

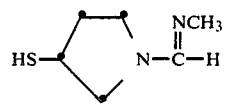

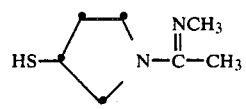

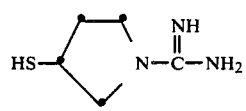

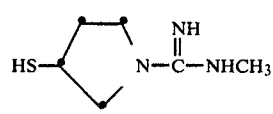

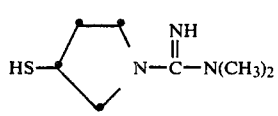

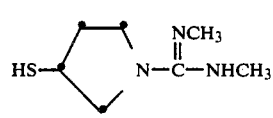

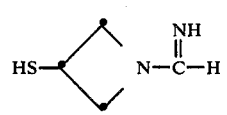

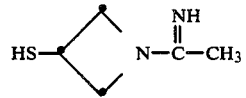

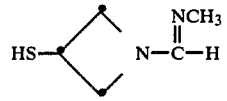

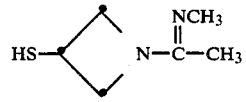

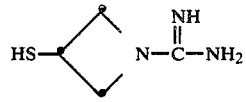

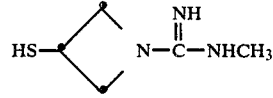

-continued
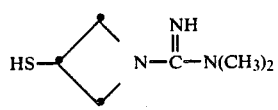
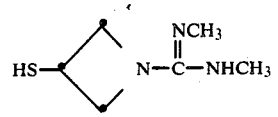
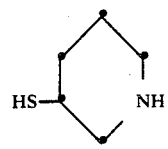
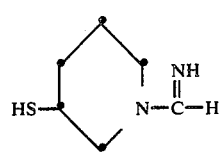
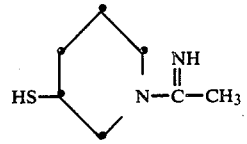
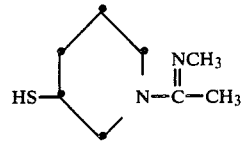
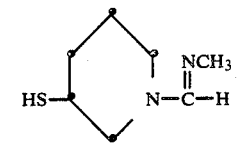
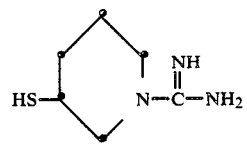
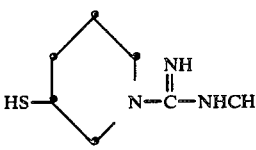
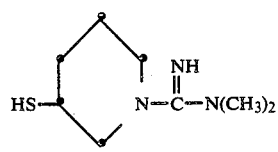
-continued
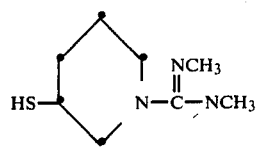
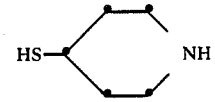
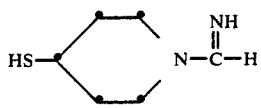
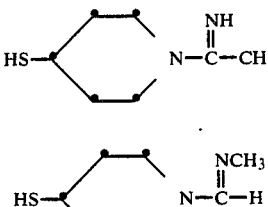
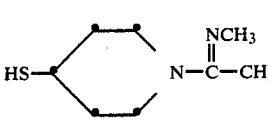
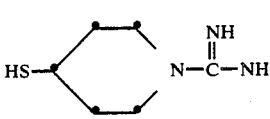
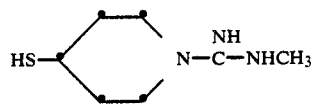
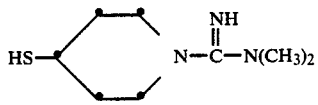
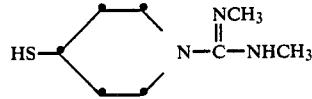
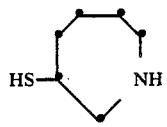
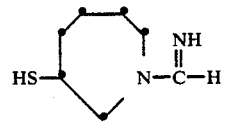

-continued

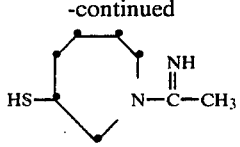

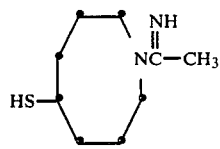

Pharmaceutically acceptable salts, I include metal salts e.g. alkali metals (Na, K), alkaline earth metals (Ca, Mg), aluminum and like; pharmaceutically acceptable esters of I are set out in more detail below and include derivatives of I where the carboxy hydrogen is replaced by $C_1$-$C_6$ alkyl, $C_3$-$C_6$ cycloalkyl, benzyl glyceryl, (5—$C_1$-$C_6$ alkyl -2-oxo-1,3 dioxolen-4-yl) methyl, pivaloxymethyl (also see U.S. Pat No. 3,938,138 for additional related groups) and the like.

Alternatively, the desirable heterocycyl amidino and guanidino 1-p-methylcarbapenems can be prepared by derivatization of a cyclic amino parent compound via amidination or quanidination reactions. The following scheme domonstrate such derivatizations.

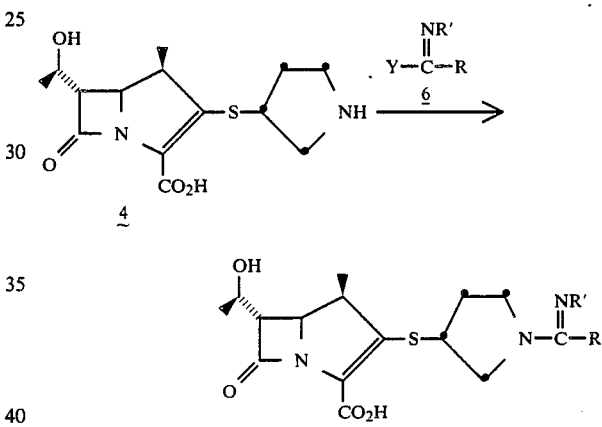

Typically, the parent compound 4 is dissolved in a buffer solution such as phosphate or MOPS buffer at 0° C. The pH of the solution is brought to 8.5 with 2.5N NaOH prior to addition of reagent 6. To the solution is added 1.0 to 1.5 equivalents of 6 and readjusted pH to 8.5 with 2.5N NaOH. After stirring at 0° C. for 10 minutes, the soution is acidifed with phosphoric acid to pH 7.0, extracted with ether. The aqueous layer is concentrated in vacuo then chromatographed by a XAD-2 column which is eluted with D.I. water to give product 5 as solid after lyophilization.

The representative reagents 6 (wherein Y is a leaving group such as halogen, OMe, OEt, $OCH_2C_6H_5$, SMe SEt, or the like; X is a anion such as halogen, $BF_4$, $SbF_6$ or the like; R' is hydrogen; $CH_3$, $C_2H_5$ or the like; and R is hydrogen, $C_3$, $C_2H_5$, $NH_2$, $NHCH_3$, $N(CH_3)_2$ or the like) are summarized in Table 1.

TABLE I

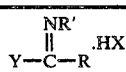.HX

| R | R' | Y | X |
|---|----|---|---|
| H | H | OEt | Cl |
| $CH_3$ | H | OEt | Cl |
| $CH_3$ | $CH_3$ | OEt | $BF_4$ |

TABLE I-continued

| R | R' | Y | X |
|---|---|---|---|
| H | CH₃ | OCH₂—⬡ | SbF₆ |
| NH₂ | H | SMe | Cl |
| NHCH₃ | H | SMe | BF₄ |
| NHCH₃ | CH₃ | SMe | SbF₆ |
| N(CH₃)₂ | H | SMe | BF₄ |
| H | (CH₃)₂ | Cl | Cl |
| H | CH₂CH₃ | OEt | Cl |

As noted above, the compounds of the present invention may also generally be represented by the following structural formula:

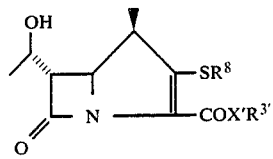 I wherein X' is oxygen, sulfur or NR" (R' is hydrogen or loweralkyl having from 1 to 6 carbon atoms); and R³' is hydrogen, or, inter alia, is representatively selected to provide the pharmaceutically acceptable salt, ester, anhydride (R³' is acyl), and amide moieties known in the bicyclic B-lactam antibiotic art; R³' may also be a readily removeable blocking group.

Identification of the Radical —COX R³'

In the generic representation of the compounds of the present invention (I, above), the radical represented by —COX'R³' is, inter alia, —COOH (X' is oxygen and R³' is hydrogen) and all radicals known to the effective as pharmaceutically acceptable ester, anhydride (R³' is acyl) and amide radicals in the bicyclic B-lactam antibiotic art, such ast the cephalosporins and penicillins and nuclear analogues thereof.

Suitable blocking esters (R³', X=O) include those selected from the following list which is representative:

(i) R³'=CRᵃRᵇRᶜ wherein at least one of RᵃRᵇ and Rᶜ is an electron-donor, e.g., p-methoxyphenyl. The remaining Rᵃ, Rᵇ and Rᶜ groups may be hydrogen or organic substituting groups. Suitable ester groups of this type include p-methoxybenzyloxcarbonyl.

(ii) R³'=CRᵃRᵇRᶜ wherein at least one of Rᵃ, Rᵇ and Rᶜ is an electron-attracting group, e.g., p-nitrophenyl, trichloromethyl, and o-nitrophenyl. Suitable esters of this type include p-nitrobenzyloxycarbonyl, and 2,2,2-trichloroethoxycarbonyl.

(iii) R³'=CRᵃRᵇRᶜ wherein at least two of Rᵃ, Rᵇ and Rᶜ group, if there is one, is hydrogen. Suitable esters of this type include t-butyloxcarbonyl, diphenylmethoxcarbonyl and triphenylmethoxycarbonyl.

Silyl esters, under this category of blocking groups, may conveniently be prepared from a halosilane of the formula: R⁴₃ Six' wherein X' is a halogen such as chloro or bromo and R⁴ is alkyl, e.g., methyl, ethyl, t-butyl.

Pharmaceutically acceptable carboxyl derivative of the present invention are those derived by reacting I with alcohols, acylating reagents and the like. For example, esters and amides of interest are the above-listed starting materials and final products having the —COX'R³' group at the 3-position; wherein X' is oxygen, sulfur or NR' (R'is H or R³'), and R³' is alkyl having 1-6 carbon atoms, straight or branched, such as methyl, ethyl, t-butyl, and the like; carbonylmethyl, including phenacyl; aminoalkyl including 2-methylaminoethyl, 2-diethylaminoethyl; alkanoyloxyalkyl wherein the alkanoyloxy portion is straight or branched and has 1-6 carbon atoms and the alkyl portion has 1-6 carbon atoms, such as pivaloyloxymethyl; haloalkyl wherein halo is chloro, and the alkyl portion is straight or branched having 1-6 carbon atoms, e.g., 2,2 2-trichloroethyl; alkenyl having 1-4 carbon atoms such as 2-propenyl, 3-butenyl, and 4-butenyl; aralkyl and lower alkoxyl- and nitro-substituted aralkyl such as benzyl, benzhydryl, o-nitrobenzyl, p-methoxybenzyl, and p-nitrobenzyl; phthalidyl; benzyloxyalkyl having 8-10 carbon atoms such as benzyloxymethyl, and (4-nitro) benzyloxymethyl.

In addition to the esters (and thio esters) listed above, amides are also embraced by the present invention i.e., wherein X' is the

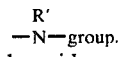
—N—group.

Representative of such amides are those wherein R' is selected from the group consisting of hydrogen and lower alkyl such as methyl and ethyl.

The most preferred —COX'R³' radicals of the present invention are those wherein (relative to Structure I above), X' is oxygen and R³' is hydrogen; loweralkyl having 1-4 carbon atoms; lower alkenyl such as 3-methylbutenyl, 4-butenyl and the like; benzyl and substituted benzyl such as p-nitrobenzyl; pivaloyloxymethyl, 3-phthalidyl; and phenacyl.

The compounds of the present invention (I) are valuable antibiotics active against various gram-positive and gram negative bacteria and accordingly find utility in human and veterinary medicine. Representative *Staphylococcus aureus, Escherichia coli, Klebsiella pneumoniae, Bacillus subtilis, Salmonella typhosa Psuedomonas* and *Bacterium proteus*. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy and inhibit the growth of harmful bacterial on medical and dental equipment and as bactericides in industrial applications, for example in water based paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup acacia, gelatin, sorbitol, tragacanth, or polyvinylpyrrolidone; fillers, for example, lactose sugar, cornstarch, calcium phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles. and may contain formulatory agents. Alternatively, the active ingredient may be in powder form for reconstitution, at the time of delivery, with a suitable vehicle, such as sterile water.

The compositions may also be prepared in suitable forms for adsorption through the mucous membranes of the nose and throat or bronchial tissues and may conveniently take the form of liquid sprays or inhalants, lozenges, or throat paints. For medication of the eyes or ears, the preparation may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention (I).

The compositions for human delivery per unit dosage, whether liquid or solid, may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution. For zwitterionic species described under Structure I, the pH of such solutions typically will correspond to the zwitterionic species described under Structure I, the pH of such solutions typically will correspond to the zwitterionic point; however, consideration of individual properties of solubility and stability may require such aqueous solutions to have a pH other than that of the zwitterionic point, for example in the range of 5.5 to 8.2.

In the foregoing word description of the above schematic reaction diagram for the total synthesis of the defined carbapenem antibiotics, it is to be understood that there is considerable latitude in selection of precise reaction parameters. Suggestion of this latitude and its breadth is generally indicated by the enumeration of equivalent solvent systems, temperature ranges, protecting groups, and range of the identities of involved reagents. Further, it is to be understood that the presentation of the synthetic scheme as comprising distinct steps in a given sequence is more in the nature of a descriptive convenience than as a necessary requirement: for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation.

The following examples demonstrate the so called "nitrogen heterocyclyl amidino and quanidino" embodiments of I. As defined above, such embodiments are charaterized by the following generic representation:

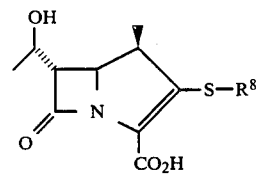

wherein $R^8$, characterized by the presence of a nitrogen heterocyclyl amindino or guanidino group, is defined above.

EXAMPLE 1

Preparation of (8R,6S,5R)-1-β-methyl-2-3'-pyrrolidylthio)-6-(1'-hydroxyethyl)-1-carbapen-2-em-3-carboxylic acid

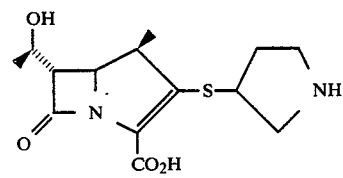

Step A

Preparation of p-nitrobenzyl (5R,6S,8R)-1-β-methyl-2-[N-(p-nitrobenzyloxycarbonyl)-3'-pyrrolidylthio]-6-(1'-hydroxethyl)-1-carbapen-2-em-3-carboxylate 3

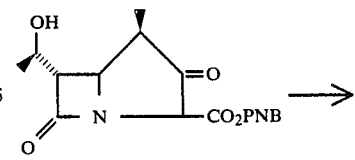

-continued

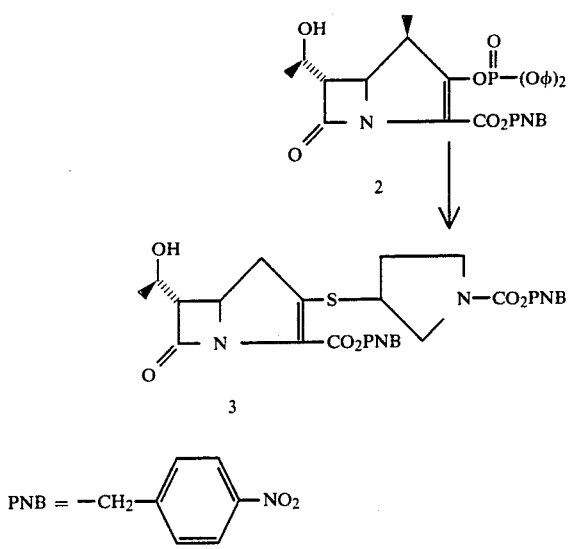

PNB = —CH₂—⟨C₆H₄⟩—NO₂

Diisopropylethylamine (50 μl) and diphenylchlorophosphate (56.7 μl) were added to an ice-cold solution of bicyclic keto ester 1 (100 mg) in acetonitrile (1.0 ml). The resulting solution was stirred in the cold and under a N₂ atmosphere for 20 minutes to effect conversion to the vinyl phosphate 2. To the solution was added N-p-nitrobenzyloxycarbonyl-3-mercaptopyrrolidine (93 mg) and diisopropylethylamine (50 μl). The resulting solution was kept in the cold for 20 hours, then diluted with ethyl acetate, washed with brine, dried over Na₂SO₄, filtered, and evaporated in vacuo to give crude product 3 which was purified by chromatography on a column of silica gel (1.5×15 cm) eluting with 30% EtOAc/cyclohexane.

Step B

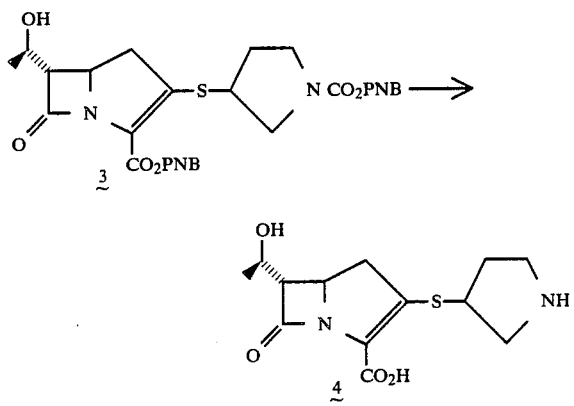

A mixture of diprotected carbapenem 3 (115 mg), THF (10 ml), ethanol (10 ml), 0.1 M pH 7 phosphate buffer (10 ml) and 10% Pd/C (58 mg) were hydrogenated at 50 psi for 2.0 hours. The mixture was filtered through a cellite pad to remove the catalyst which was washed with 10 ml water. The filtrate was extracted with 2×50 ml ethyl acetate, concentrated under vacuum to 5 ml. and loaded onto a Dowex-50×4 Na⁺cycle) column (2.2×10 cm). The column was eluted with water to give 4 as solid after lyophilization.

EXAMPLE 2

Preparation of (8R,6S,5R)-1-2-(N-acetimidoyl-3'-pyrolidylthio)-6-(1'-hydroxyethyl)-1-carbapen-2-em-3-carboxylic acid

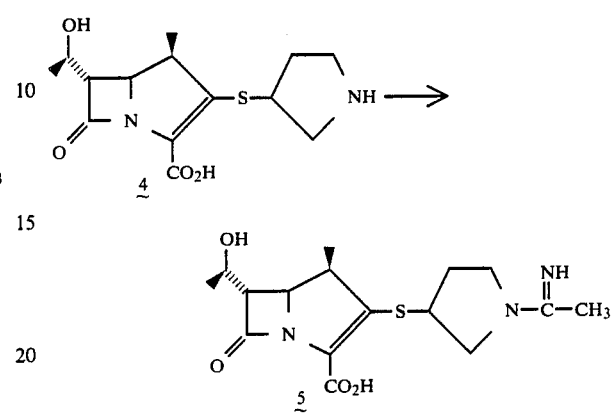

At 0° C., the free amine 4 (100 mg) was dissolved in 10 ml 0.1 M pH 7.0 phosphate buffer. The solution was brought to pH 8.5 with 2.5 N NaOH prior to addition of ethyl acetimidate hydrochloride (400 mg). The pH was readjusted to 8.5 with 2.5 N NaOH after imidate was added. The mixture was stirred in the cold for 10 minutes then acidified with phosphoric acid to pH 7.0, extracted with ethyl acetate. The aqueous layer was separated, concentrated to 5 ml volume and chromatographed by a Dowex-50×4 (Na⁺cycle) column (2.2×10 cm). The column was eluted with D.I. water to give 5 as solid after lyophilization.

EXAMPLE 3

Following the procedure of Example 2 except replacing acetimidate with another imidate reagents, products (1) to (3) were obtained.

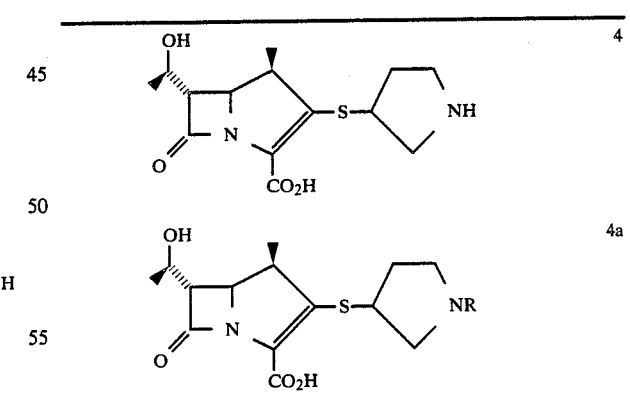

| Products of Formula 4a | Reagents | |
|---|---|---|
| (1) R = —C(=NH)—H | EtO—C(=NH)—H | .HCl |
| (2) R = —C(=NCH₃)—CH₃ | EtO—C(=NCH₃)—CH₃ | .HCl |
| (3) R = —C(=NCH₃)—H | EtO—C(=NCH₃)—H | .HBF₄ |

EXAMPLE 4

Preparation of
(8R,6S,5R)-1-β-methyl-2-(N-guanyl-3'-pyrrolidyl)-6-(1'hydroxyethyl)-1-carbapen-2-em-3-carboxylic acid 7

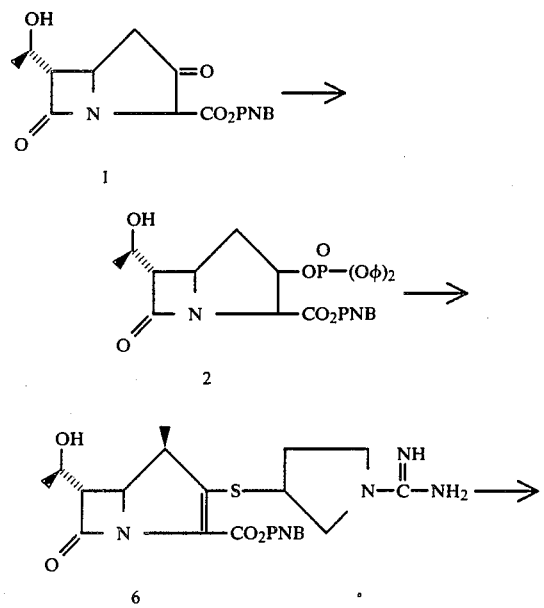

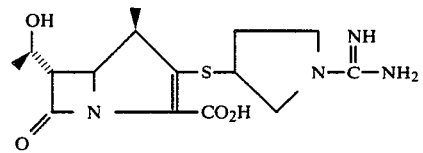

The bicyclic keto ester 1 (33 mg) dissolved in acetonitrile (0.47 ml) at 0° C. under $N_2$ atmosphere was treated with diphenyl chlorophosphate (21 μl) and diisopropylethylamine (20 μl) for 30 minutes to form 2. The mixture containing 2 was cooled to −35° C. in an ethylene glycol-water-dry ice bath then treated with DMSO solution of N-guanyl-3-mercaptopyrrolidine hydrochloride (20 mg) and diisopropylethylamine (20 μl) for 30 minutes. The mixture was diluted with 5 ml ether and centrifuged to precipitate oil product 6. The crude product 6 was redissolved in THF (3.72 ml) and 0.1 M pH 7.0 phosphate buffer (2.80 ml) and hydrogenated at 50 psi hydrogen in the presence of 50 mg of 10% Pd/C at room temperature for 1 hour, then filtered from catalyst. The filtrate was extracted with ether, concentrated to 4 ml and charged to a Dowex-50×4 ($Na^+$cycle) column (2.2×6 cm) which was eluted with D.I water to give product 7 as solid after lyophilization.

EXAMPLE 5

Following the procedure of Example 4 except replacing N-guanyl-2-mercapto-pyrrolidine with another mercaptan, products (1) to (17) were obtained.

-continued

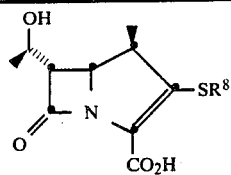

I

| Formula I Products R⁸ | Mercaptans Reactant |
|---|---|
| (6) ![structure] N—C(=NH)—H | HS—[ring]—N—C(=NH)—H·HBF₄ |
| (7) ![structure] N—C(=NH)—CH₃ | HS—[ring]—N—C(=NH)—CH₃·HBF₄ |
| (8) ![structure] N—C(=NH)—NH₂ | HS—[ring]—N—C(=NH)—NH₂·HBF₄ |
| (9) ![structure] NH | HS—[ring]—NH·HClOₓ |
| (10) ![structure] N—C(=NH)—H | HS—[ring]—N—C(=NH)—H·HBF₄ |
| (11) ![structure] N—C(=NH)—CH₃ | HS—[ring]—N—C(=NH)—CH₃·HBF₄ |
| (12) ![structure] N—C(=NH)—NH₂ | HS—[ring]—N—C(=NH)—NH₂·HSbF₆ |
| (13) ![structure] NH | HS—[ring]—NH·HCl |
| (14) ![structure] N—C(=NH)—H | HS—[ring]—N—C(=NH)—H·HBF₄ |
| (15) ![structure] N—C(=NH)—CH₃ | HS—[ring]—N—C(=NH)—CH₃·HClO₄ |

| Formula 1 Products R[8] | Mercaptans Reactant |
|---|---|
| (16) ![cycle with N-C(=NH)-H substituent] | ![HS-cycle with N-C(=NH)-H·HBF4 substituent] |
| (17) ![pyrrolidine with N-C(=NH)-H substituent] | ![HS-pyrrolidine with N-C(=NH)-H substituent] |

EXAMPLE 6

Preparation of (N-p-nitrobenzyloxycarbonyl-3-mercapto-pyrrolidine

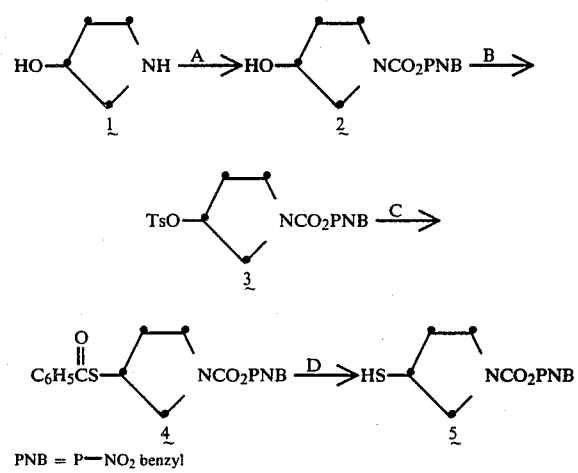

PNB = P—NO$_2$ benzyl

Step A: Preparation of N-p-nitrobenzyloxycarbonyl-3-hydroxypyrrolidine (2)

At 0° C., 3-hydroxypyrrolidine 1 (2.0 g) was dissolved in 50 ml of dioxane-water (1:1) solution. The pH of the solution was kept at 8.0 with 1.0 N NaOH while a dioxane solution of p-nitrobenzylchloroformate (4.5 g) was added. The mixture was stirred for 1 hour, then extracted with ethyl acetate. The organic layer was washed thoroughly with water, brine then dried over Na$_2$SO$_4$. Evaporation of solvent in vacuo gave Product 2.

Step B: Preparation of N-p-nitrobenzyloxy carbonyl-3-p-toluenesulfonyloxy-pyrrolidine (3)

Pyrrolidine 2 (0.65 g) was dissolved in 20 ml CH$_2$Cl$_2$. To the solution was added p-toluenesulfonyl chloride (0.70 g) and triethylamine (0.6 ml). The mixture was stirred at room temperature overnight then diluted with CH$_2$Cl$_2$ and washed with 5% NaHCO$_3$, water and brine. The organic layer was separated, dired over Na$_2$SO$_4$, and evaporated in vacuo to give 3.

Step C: Preparation of N-p-nitrobenzyloxycarbonyl-3-benzoylthio-pyrrolidine (4)

To a stirred toluene (2 ml) solution of 3 (0.35 g) and thiolbenzoic acid (0.14 g) is added 1.5-diazabicyclo[5.4.-0]undec-5-ene (DBU) (0.2 g). The mixture was stirred and heated at 80° C. for 3 hours. After cooling to room temperature, the solution was diluted with 50 ml toluene and washed with saturated NaHCO$_3$. The organic layer was separated, dried over Na$_2$SO$_4$ and evaporated in vacuo to give product 4.

Step D: Preparation of N-p-nitrobenzyloxycarbonyl-3-mercapto-pyrrolidine (5).

The pyrrolidine 4 (0.39 g) in 12 ml THF was treated with LiBH$_4$ (0.15 g) at 0° C. for 1 hour. The mixture was hydrolyzed with 0.5 N HCl and extracted with ethyl acetate. The organic layer was separated, washed with water, brine, dried over Na$_2$SO$_4$ then evaporated in vacuo to give Product 5.

EXAMPLE 7

Following the procedure of Example 6 except replacing the starting material with another hydroxyl substituted cyclic amine, Products (1) to (4) were obtained.

| Starting Material | Product |
|---|---|
| (1) HO-⬡-NH | HS-⬡-NCO$_2$PNB |
| (2) HO-⬡-NH | HS-⬡-NCO$_2$PNB |

-continued

| Starting Material | Product |
|---|---|
| (3) HO–⟨⟩–NH | HS–⟨⟩–NCO₂PNB |
| (4) HO–⟨⟩–NH | HS–⟨⟩–NCO₂PNB |

EXAMPLE 8

Preparation of N-quanyl-3-mercaptopyrrolidine

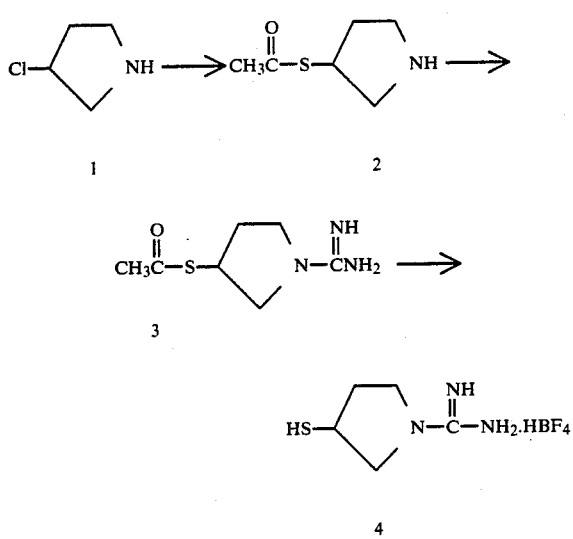

Step A: Preparation of 3-(S-acetylthio)pyrrolidine 2

3-Chloro-pyrrolidine 1 was prepared according to a known procedure (British patent No. 1,042,894).

The starting material 1 (1.05 g) was dissolved in 5 ml DMF and treated with sodium thiolacetate (0.5 g) at 60° C. for 6 hours. The mixture was diluted with 20 ml ethyl acetate and washed with 10% NaHCO₃, water and brine. The organic layer was separated, dried over Na₂SO₄ then evaporated in vacuo to give Product 2.

Step B: Preparation of N-quanyl-3-mercaptopyrrolidine tetrafluoroborate 4

The 3-(S-acetylthio)pyrrolidine 2 (1.45 g) was dissolved in 5 ml DMF and treated with 2-methyl-2-thiopseudourea sulfate (0.56 g) and triethylamine (0.4 ml) at room temperature for 16 hours. The mixture was hydrolyzed with water (5 ml). Adjusted to pH 10 with 1N NaOH at 0° C. After 30 minutes reaction, the mixture was acidified with HBF₄ to pH 2.0 and extracted with ethyl acetate. The aqueous layer was separated and mixed with methanol to precipitate the product. The crude product was purified by crystallization from hot ethanol.

EXAMPLE 9

Preparation of N-imidoyl-3-mercaptopyrrolidine hydrochloride

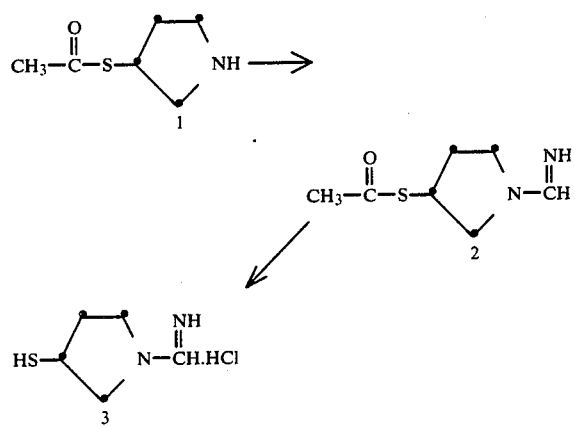

The 3-(S-acetylthio)pyrrolidine 1 (1.45 g) in 5 ml DMF was treated with O-ethyl formimidate hydrochloride (0.5 g) and triethylamine (0.4 ml) at room temperature for 6 hours. The mixture was hydrolyzed with 0.1N NaOH (5 ml) at 0° C. for 30 minutes then acidified with HCl to pH 2.0 and extracted with ethyl acetate. The aqueous layer was separated and mixed with methol to precipitate product 3 which was purified by crystallization from methanol-H₂O.

EXAMPLE 10

Following the procedures of Examples 8 and 9, except replacing 3-chloropyrrolidine with the desirable starting cyclic amine and N-derivatizing agent, the mercaptans used in Examples 4 and 5 were obtained.

EXAMPLE 11

STEP A 1-p-nitrobenzyloxycarbonyl-4-hydroxy-piperidine

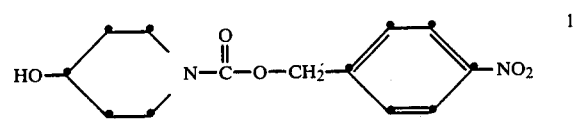

To a stirred solution of 4-hydroxypiperidine (1.01 g, 10 mm) and 4-dimethylaminepyridine (1.22 g, 10 mm) in EtOAc (30 ml) and water (20 ml) cooled to 0° is added a solution of p-nitrobenzyloxycarbonyl chloride (2.15 g, 10 mm) in EtOAc 50 ml. After stirring for 50 minutes, the organic phase is separated and washed with water, dried and evaporated. The residue is chromatographed on silica gel using CHCl₃/MeOH to give the desired product 1.

STEP B
1-p-nitrobenzyloxycarbonyl-4-methanesulfonyloxypiperidine

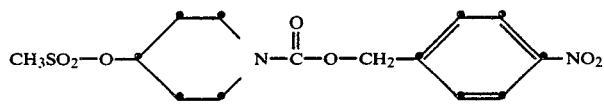

A mixture of 1 (2.8 g, 10 mm), Et₃N (2.02 g, 20 mm) in CH₂Cl₂ 20 ml cooled to 0° is treated with methane sulfonyl chloride (228 g, 20 mm) and the mixture is stirred at 0° for 1 hour at room temperature for 3 hours. The reaction mixture is diluted with methylene chloride washed with 5% NaHCO₃ solution, water and brine, then dried and evaporated to give a residue which is chromatographed on silica gel to give the desired 2.

STEP C
1-p-Nitrobenzyloxycarbonyl-4-benzoylthiopiperidine

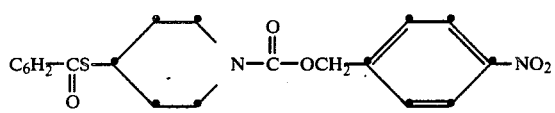

To a stirred solution of 2 (3.58 g, 10 mm) and thio benzoic acid (1.38 g, 10 mm) in toluene (20 ml) is added 1,5-diazabicyclo[5.4.0]undec-5-ene (DBV) (1.7 g, 11 mm). After stirring for 3 hours at 80° the reaction mixture is diluted with EtOAc, washed with saturated NaHCO₃, dried and evaporated to give crude 3 which is purified by chromatography.

STEP D
1-p-nitrobenzyloxycarbonyl-4-mercaptopiperidine

To a stirred solution of 3 (2.0 g, 5 mmol) in THF (50 ml) is added LiBH₄ (1.0 g excess) at 0° under N₂. After stirring 1 hour at 0° the reaction mixture is acidified with 5% HCl, diluted with EtOAc (200 ml) washed with water, brine and dried. The solvent is removed under reduced pressure and the residue is chromatographed on silica gel to give 4.

STEP E

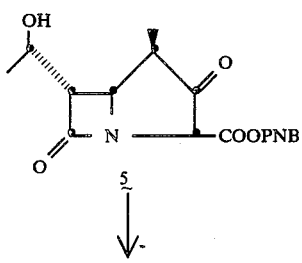

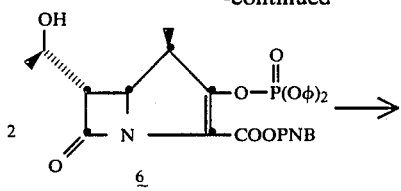

p-nitrobenzyl(5R, 6S)-2-[(RS)-N-p-nitrobenzyloxycarbonyl)-4-piperidylthio]-6-[(R)-1-hydroxyethyl]-1-(R)-methyl-1-carbarbapen-2-em-3-carboxylate N,N-Diisopropylamine (79 ml, 0.46 mmol) and diphenylchlorophosphate (88 mg, 0.42 mmol) are added to an ice-cold solution of bicyclic keto ester 5 (150 mg, 0.42 mmol) in CH₃CN (3.0 ml). The resulting solution is stirred in the cold, under N₂ for 40 minutes to affect conversion to the vinyl phosphate 6.

The solution is treated with i-Pr₂NEt (79 mg, 0.40 mmol) and with a solution of mercaptan 4 (120 mg, 0.45 mmol). The resulting solution kept at 0° overnight then diluted with EtOAc, washed with brine, dried over MgSO₄ and evaporated to give the crude 7 which is purified by preparation t.l.c. on silica gel plates. Compound 7 obtained is a mixture of two diastereomers which are isomeric at the chiral center of the the side chain.

STEP F

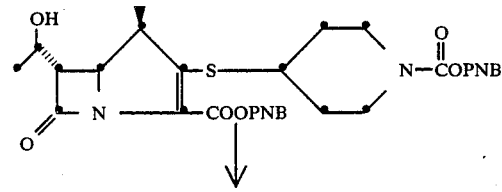

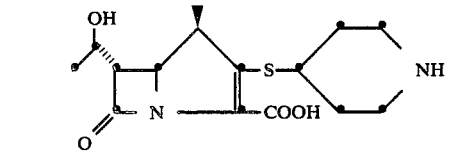

(5R, 6S)-2-(4-piperidinylthio)-1-(R)-methyl-1-carbapen-2-em-3-carboxylic acid 8

At mixture 7 (51 mg), PtO₂ (29 mg), THF (10 ml), H₂O (5 ml) and 0.1M (pH 7 MOPS buffer (1 ml) is stirred under H₂ at room temperature for 45 minutes. The catalyst is filtered and washed with water. The filtrate and washings were extracted with EtOAc and Et₂O, concentrated under vacuum and freeze dried to give 8.

EXAMPLE 12

Starting with 3-hydroxypiperidine and following the Steps A to F of Example 11, one obtains (1R, 5R, 6S)-2-[(RS)-piperidinylthio)-6-[(R)-1-hydroxyethyl]-1-methyl-1-carbapen-2-em-3-carboxylic acid.

The two isomers at the thio side chain can be separated by reversed phase HPLC on a C-18 bondpack column to give (1R, 5R, 6S)-2-[(R)-3-piperidinylthio)-6-[(R)-1-hydroxyethyl]-1-methyl-1-carbapen-2-em-3-carboxylic acid and (1R, 5R, 6S)-2-[(S)-3-piperidinylthio)-6-[(R)-1-hydroxyethyl]-1-methyl-1-carbapen-2-em-3-carboxylic acid.

EXAMPLE 13

Starting with 3-hydroxypyrrolidine and following steps A to F of Example 11, one obtains (1R, 5R, 6S)-2-[(RS)-3-pyrrolidinylthio]-6-[(R)-1-hydroxyethyl]-1-methyl-1-carbapen-2-em-3-carboxylic acid.

EXAMPLE 14

Starting with the bicyclic keto ester 5 and following the procedures of Steps E and F of Example 11 and using the appropriate mercaptans (HSR⁸), one obtains the desired products 9

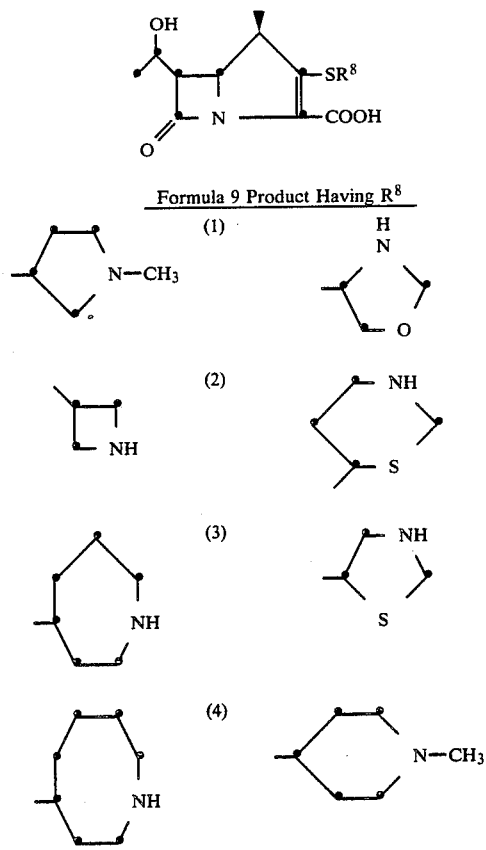

EXAMPLE 15

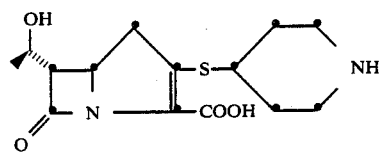

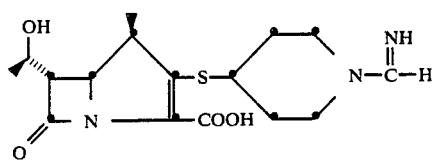

(1R, 5R, 6S)-2-[(RS)-N-formimidoyl-4-piperidinylthio]-6-[(R)-1-hydroxyethyl]-1-methyl-1-carbapen-2-em-3-carboxylic acid 10

A solution of the amine 8 (11 mg, 0.038 mmol) in H₂O (2 ml) containing MOPS buffer is cooled to 0° with stirring. The pH of the solution is brought to 8.5 with 0.025N NaOH. Methyl formimidate hydrochloride (55 mg, 0.58 mmol) is added and the pH readjusted to 8.5 and the solution is stirred in the cold for 10 minutes. The solution is brought to pH 7 diluted with water, extracted with EtOAc and evaporated to a small volume and placed on a reversed phase plate elution with 5% THF/H₂O and extraction from the plate using 20% H₂O/CH₂CN gives the product 10.

EXAMPLE 16

Starting with the appropriate amino acid products of Example 13 and following the procedure of Example 14, one obtains the corresponding formimidines of the amino acid of Example 13.

EXAMPLE 17

Starting with the amino acid product (8) of Example 13 and following the procedure of Example 14 but substituting methyl acetimidate hydrochloride instead of methyl formimidate hydrochloride one obtains (1R, 5R, 6S)-2-[(RS)-N-acetimidoyl-4-piperidinylthio]-6[(R)-1-hydroxyethyl]-1-methyl-1-carbpen-2-em-3-carboxylic acid.

EXAMPLE 18

Starting with the appropriate amino acid products of Example 13 and following the procedure of Example 14 one obtains the corresponding acetamidines of the amino acid products of Example 13.

EXAMPLE 19

STEP A

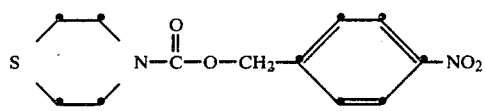

1-p-nitrobenzyloxycarbonylthiomorpholine

Starting with thiomorpholine and treating it with p-nitrobenzyloxycarbonylchloride as in Step A of Example 6, 1-p-nitrobenzyloxycarbonylthio-morpholine 1 is obtained.

STEP B

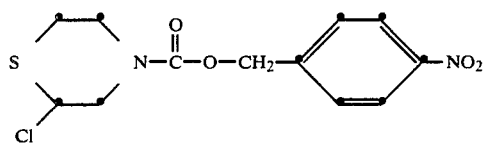

1-p-nitrobenzyloxycarbonyl-3-chloro-thiomorpholine

To a stirred solution of 1 (2.82 g, 10 mmol) in CHCl$_3$ (15 ml) is added N-chlorosuccinimide (1.5 g, 11 mmol) at room temperature under N$_2$. The reaction mixture is stirred for 15 minutes and the solvent is removed under reduced pressure at 0°. The residue which is 2 is used without purification in the next step.

STEP C

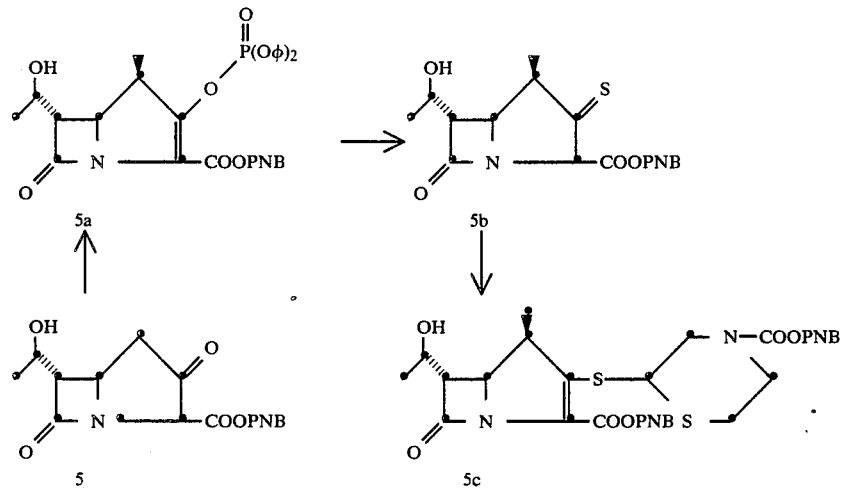

p-Nitrobenzyl(8R,5R,6S)-2-[(RS)-N-p-nitrobenzyloxycarbonyl-3-thiomorpholinylthio)-6-[(R)-1-hydroxyethyl]-1-β-methyl-1-carbapen-2-em-3-carboxylate To a solution of the bicyclic ketone 5 (36 mg) in CH$_3$CN (2 ml) cooled to 0° under N$_2$ is added i-Pr$_2$NEt (19/µl) followed by diphenyl chlorophosphate (22/µl). The mixture (containing 5a) is stirred for 1 hour. The solvent is removed under reduced pressure and the residue is dissolved in DMF (1 ml) and cooled to 0°. Sodium hydrosulfide (5.6 mg) in DMF (0.6 ml) is added followed by i-Pr$_2$NEt (19/µl). The mixture (containing 5b) is stirred at 0° for 25 minutes and treated with a solution of 1-p-nitrobenzyloxy-carbonyl-3-chlorothiomorpholine (30 mg) in DMF (1 ml) followed by i-Pr$_2$NEt (19/µl). The reaction mixture is stirred for 1 hour at 0°, diluted with EtOAc washed with water, 5% NaHCO$_3$ solution, saturated NaCl then dried and evaporated to give a residue which is chromatographed on silica gel to give 5c.

STEP D (1R, 5R, 6S)-2-[(RS)-3-thiomorpholinethio]-6-[(R)-1-hydroxyethyl]-1-methyl-1-carbapen-2-em-3-carboxylic acid

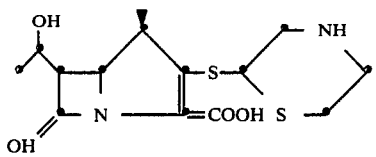

The product 5c is treated under the reaction conditions of Step F, Example 11 to give the product 5d.

EXAMPLE 20

Starting with thiazolidine and following the steps A to D of Example 19 one obtains: (1R, 5R, 6S)-2-[(RS)--2-thiazolidinethio]-6-[(R)-1-hydroxyethyl]-1-methyl-1-carbapen-2-em-3-carboxylic acid of the formula

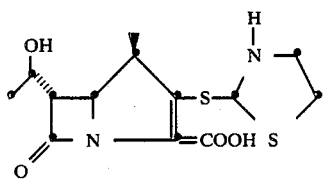

Claims to the invention follow.
What is claimed is:
1. A compound having the formula:

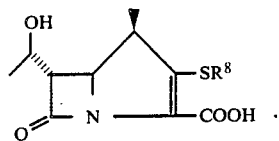

and pharmaceutically acceptable salts and esters thereof, wherein $R^8$ is

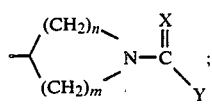

and wherein n is 1 or 2 and m is 1; X is —NR; and Y is —R; and wherein R is hydrogen or methyl.

2. A pharmaceutical composition for antibacterial use comprising a pharmaceutically acceptable carrier and an antibacterially effective amount of a compound of claim 1.

3. A method of treating bacterial infections in animals and humans which comprises administering a therapeutically effective amount of compound of claim 1.

4. A compound of claim 1 wherein $R^8$ is:

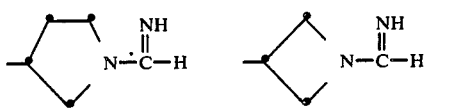

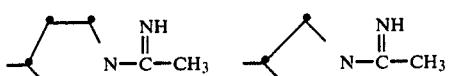

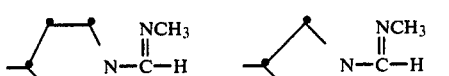

* * * * *